United States Patent
Chen et al.

(10) Patent No.: US 8,026,559 B2
(45) Date of Patent: Sep. 27, 2011

(54) BIOSENSOR DEVICES AND METHOD FOR FABRICATING THE SAME

(75) Inventors: I-Hsiu Chen, Taipei (TW); Chung-Jung Hsu, Hsinchu (TW)

(73) Assignee: VisEra Technologies Company Limited, Hsinchu (TW)

( * ) Notice: Subject to any disclaimer, the term of this patent is extended or adjusted under 35 U.S.C. 154(b) by 41 days.

(21) Appl. No.: 12/626,806

(22) Filed: Nov. 27, 2009

(65) Prior Publication Data
US 2011/0127619 A1 Jun. 2, 2011

(51) Int. Cl.
*H01L 27/14* (2006.01)
(52) U.S. Cl. . 257/414; 257/443; 257/448; 257/E27.129; 438/49
(58) Field of Classification Search ............... 257/414, 257/443, 448, E27.129; 438/49
See application file for complete search history.

(56) References Cited

U.S. PATENT DOCUMENTS
7,425,749 B2 * 9/2008 Hartzell et al. ............... 257/414
* cited by examiner

*Primary Examiner* — Tu-Tu Ho
(74) *Attorney, Agent, or Firm* — Muncy, Geissler, Olds & Lowe, PLLC

(57) ABSTRACT

A biosensor device is provided, including a first semiconductor layer formed over an interconnect structure. A plurality of detection elements are formed in the first semiconductor layer. An optical filter layer is formed over and physically contacts the first semiconductor layer. A second semiconductor layer is formed over the optical filter layer, having opposing first and second surfaces, wherein the first surface physically contacts the optical filter layer. A plurality of isolation walls are formed over the second semiconductor layer from the second surface thereof, defining a plurality of micro-wells over the second semiconductor layer, wherein the isolation walls and the second semiconductor layer comprises the same material, and the micro-wells are correspondingly arranged with the detection elements. An immobilization layer is formed over the second semiconductor layer exposed by the micro-wells and a plurality of capture molecules are formed over the immobilization layer in the micro-wells.

19 Claims, 5 Drawing Sheets

BIOSENSOR DEVICES AND METHOD FOR FABRICATING THE SAME

BACKGROUND OF THE INVENTION

1. Field of the Invention

The present invention relates to biosensor devices, and in particularly to biosensor devices with robust micro-well structures and detection elements capable of receiving light illumination from the back side of a substrate therein, and methods for fabricating the same.

2. Description of the Related Art

There exists a need in the biological field, for reliable, low cost analytical devices that allow for the rapid separation and detection of micro quantities of cellular tissue, genetic material, and organic molecules, and sequencing, etc. for use in research as well as in the diagnosis of disease(s) or the existence of certain predetermined conditions. A biological analysis device, such as a DNA analysis device, is effective for detecting and identifying viruses, bacteria, and other microbes and is essential for identifying genetic disorders. The ability to detect DNA with a high level of specificity entails high resolution separation of RNA or DNA fragments, appropriate labeling chemistry for such fragments and the adaptation of high sensitivity sensors that are specific for the labeling chemistry employed. DNA probe technology is essential for revealing the presence of diagnostically significant cells, whether they are diseased cells from a subject or infectious micro organisms.

Demand for miniaturized biological analysis devices have grown in line with demand for miniaturized electronic devices. Many of the same technological principles that have led to smaller and smaller micro processor devices have led to developing functions of a chemistry lab into a device, and then shrinking the device to the size of a US dime. For biosensor devices, the purpose of the technological principles is to develop a biosensor device that has different, discreet areas that are sensitive to different genetic sequences. These areas, or probes, are formed using a number of techniques, including photo patterning methods, such as photolithography, which is also commonly used in fabricating of micro processors. Additionally, micro machining methods, where tiny channels are machined into a chip to hold various test media, and other methods of precisely depositing test media upon chips are used in a precisely defined pattern.

BRIEF SUMMARY OF THE INVENTION

Biosensor devices and methods for fabricating the same are provided.

An exemplary biosensor device comprises a first semiconductor layer formed over an interconnect structure. A plurality of detection elements are formed in the first semiconductor layer. An optical filter layer is formed over and physically contacting the first semiconductor layer. A second semiconductor layer is formed over the optical filter layer, having opposing first and second surfaces, wherein the first surface physically contacts the optical filter layer. A plurality of isolation walls are formed over the second semiconductor layer from the second surface thereof, defining a plurality of micro-wells over the second semiconductor layer, wherein the isolation walls and the second semiconductor layer comprises the same material, and the micro-wells are correspondingly arranged with the detection elements. An immobilization layer is formed over the second semiconductor layer exposed by the micro-wells and a plurality of capture molecules are formed over the immobilization layer in the micro-wells.

Another exemplary biosensor device comprises an interconnect structure and a bulk semiconductor substrate formed over the interconnect structure, having opposing first and second surfaces, wherein the first surface physically contacts the interconnect structure. A plurality of detection elements are formed in the first semiconductor layer from the first surface thereof. A plurality of isolation walls are formed over the second surface of the first semiconductor layer, defining a plurality of micro-wells over the first semiconductor layer, wherein the isolation walls and the first semiconductor layer comprises the same material, and the micro-wells are correspondingly arranged with the detection elements. An optical filter layer is conformably formed over the isolation walls and the second surface of the first semiconductor layer. An immobilization layer is formed over a portion of the optical filter layer exposed by the micro-wells. A plurality of capture molecules are formed over the immobilization layer in the micro-wells.

An exemplary method for fabricating a biosensor device comprises providing a semiconductor on insulator (SOI) substrate comprising a first semiconductor layer, an insulating layer, and a second semiconductor layer, wherein the second semiconductor layer has an opposing first surface and second surface, and the first surface of the first semiconductor layer physically contacts the insulating layer. A plurality of detection elements are formed in the first semiconductor layer. An interconnect structure is formed over of the first semiconductor layer, covering the detection elements. The second semiconductor layer of the SOI substrate is thinned from the second surface thereof, forming a thinned second semiconductor layer. The thinned second semiconductor layer is patterned to form a plurality of isolation walls therein, thereby defining a plurality of micro-wells over the thinned second semiconductor layer. An immobilization layer is formed over the thinned second semiconductor layer exposed by the micro-wells. A plurality of capture molecules is formed over the immobilization layer in the micro-wells.

An exemplary method for fabricating a biosensor device comprises providing a semiconductor substrate comprising a bulk semiconductor material, wherein the semiconductor substrate has opposing first and second surfaces. A plurality of detection elements is formed in the semiconductor substrate from the first surface thereof. An interconnect structure is formed over of the semiconductor substrate to cover the light-sensing device. The semiconductor substrate is thinned from the second surface thereof to form a thinned semiconductor substrate. The thinned semiconductor substrate is patterned to form a plurality of isolation wall elements therein, thereby defining a plurality of micro-wells over the thinned semiconductor substrate. An optical filter layer is conformably formed over the thinned semiconductor substrate and covering the isolation wall elements. An immobilization layer is formed over the optical filter layer exposed by the micro-wells. A plurality of capture molecules is formed over the immobilization layer.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
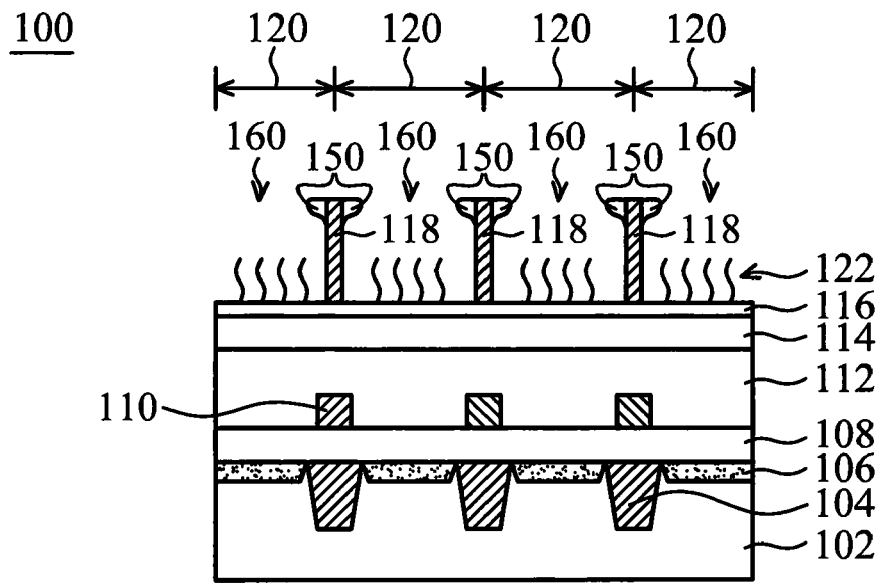
FIG. 1 is a cross section showing a biosensor device according to an embodiment of the invention.

FIG. 1 shows a schematic cross section of a biosensor device 100 known to the inventors. The biosensor device 100 is not prior art for the purpose of determining the patentability of the invention. It is merely used to show problems found by the inventors.

As shown in FIG. 1, the biosensor device 100 includes a semiconductor substrate 102 having a plurality of isolation regions 104 formed therein, thereby defining a plurality of detection regions 120 over the semiconductor substrate 102. A detection element 106 such as a photodiode is correspondingly formed in the semiconductor substrate 102 in each of the detection regions 120. For the sake of convenience, active elements such as transistors, which may be required for each of the detection elements 106, is not depicted in the drawings. An interconnect structure comprising a dielectric layer 112 and a plurality of conductive elements 110 which are respectively provided on or between at predetermined locations in consideration of electrically connection to the underlying detection elements 106 so that light (not shown) projected on the detection elements 106 will not be shielded by the existence of the conductive segments therein. In addition, an optical filter layer 114 is formed on the dielectric layer 112. An immobilization layer 116 is formed over the optical filter layer 114 to immobilize capture molecules. A plurality of isolation walls 118 is formed over the immobilization layer 116 to define a plurality of micro-wells 160 over the semiconductor substrate 102, which are correspondingly arranged with the detection regions 120, respectively. A plurality of capture molecules 122 is provided and immobilized on the surface of the immobilization layer 116 exposed by the micro-wells 160.

In one embodiment, the detection elements 106 are capable of detecting light of a first wavelength range. The capture molecules 122 can be, for example, DNA half strands, nucleic acids, peptides, or proteins which are capable of attaching molecules with predetermined markers such as fluorescence markers in a sample solution. The optical filter layer 114 may function as a bandpass filter. The isolation walls 118 for defining the micro-wells 160 can be made of photosensitive materials such as organic photoresist materials, and can be thus formed by methods such as a photolithography process.

The operation of the biosensor device 100 is described as below. During biological analysis, the biosensor device 100 is brought in contact with a sample solution comprising molecules such as DNA half strands, nucleic acids, peptides, or proteins with predetermined markers such as fluorescence markers. The fluorescence markers can be determined by wavelength analysis of the fluorescence light reemitted by the fluorescence markers. After the molecules with predetermined markers such as fluorescence markers are attached to the capture molecules 122, the micro-wells 160 of the biosensor device 100 would be projected by emission light (not shown) of a second wavelength range. Thereafter, the capture molecules 122 attached with the molecules with predetermined markers such as fluorescence markers would reemit fluorescence light of a third wavelength range after excitation thereof by the emission light of the second range. Both of the emission lights of the second wavelength range and the reemitted fluorescence light of the third wavelength range are radiated in and pass through the transparent immobilization layer 116 and pass to the optical filter layer 114. The optical filter layer 114 functions as a blocking filter for the emission light of the second wavelength range. Thus, the reemitted fluorescence light of the third wavelength range is transmitted through the optical filter layer 114 and passes through the transparent passivation layer 112 and the ILD layer 108, so that the reemitted fluorescence light may finally pass to the detection elements 106 arranged below the micro-wells 160 containing the capture molecules 122 attached with molecules with fluorescence markers. The detection elements 106 then detect the reemitted fluorescence light of the third wavelength range, wherein the detected reemitted fluorescence light of the third wavelength range is within the first wavelength range. As a result, a degree of molecular combinations are detected since the intensity of the detected fluorescence light corresponds to the number of detected molecular combinations. Emission light having the second wavelength range does not pass through the optical filter layer and cannot be detected in the detection elements 106. Thus, the primary emission light of the second wavelength range does not penetrate to the detection elements 106, unlike that of the reemitted light to be detected of the third wavelength range.

Figure 2:
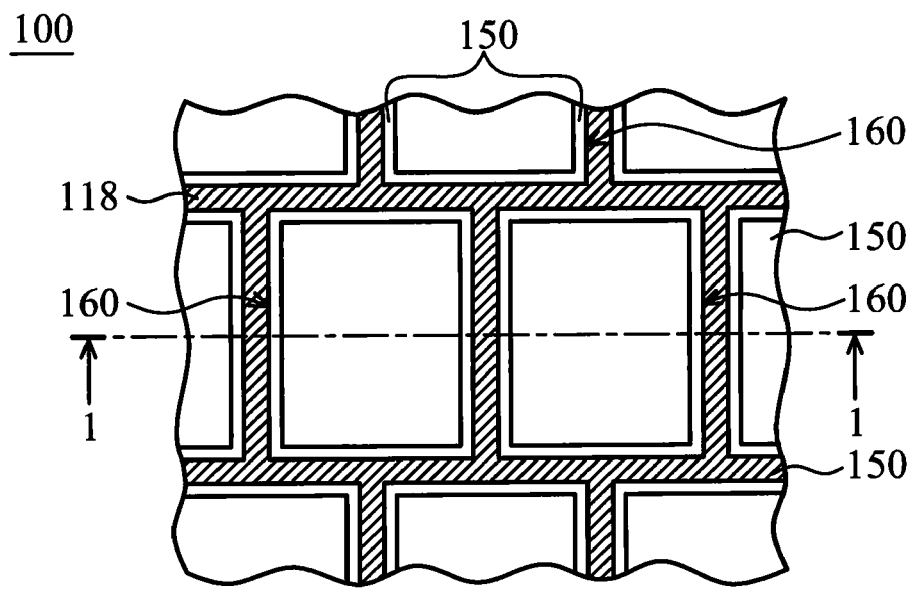
FIG. 2 is a plan view of the biosensor device illustrated in FIG. 1

The biosensor device 100 has the following drawbacks. To begin, when the size of the biosensor device 100 is reduced, pitches between and widths of isolations walls 118 of the semiconductor substrate 102 are also correspondingly reduced. However, residue overhang 150, containing organic photoresist material, may remain around a top portion of the isolation walls 118 of the semiconductor substrate 102 after formation thereof. FIG. 2 is a plan view showing the biosensor device 100 shown in FIG. 1 having residue overhangs 150 formed around the isolation walls 150 of each of the micro-wells 160. The micro-well regions 160 shown in FIG. 2 are formed with a rectangular shape but not limited thereto. The micro-well regions 160 can be formed in other polygonal shapes rather than the rectangular shape. The residue overhangs 150 shown in FIGS. 1 and 2 reduce an area of the micro-wells 120 for receiving emission light of a second wavelength range provided by a light source (not shown), thereby affecting illumination efficiency of the emitted light and fluorescence light collection efficiency of the detection elements 106. Moreover, due to the reduced size, the photoresist materials of the isolation walls 118 have weaker mechanical strength and sometimes collapse when a sample solution flows therein. When an isolation wall 188 collapses, cross-talk may occur in the corresponding detection elements 106 due to inaccurate fluorescence light collections. Accordingly, a need exists for an improved biosensor device and method for manufacturing the same, wherein the biosensor device can be fabricated with robust micro-well structures and high fluorescence light collection efficiency.

FIGS. 3-6 are schematic cross sections showing an exemplary method for fabricating a biosensor device with robust micro-well structures and high fluorescence light collection efficiency.

Figure 3:
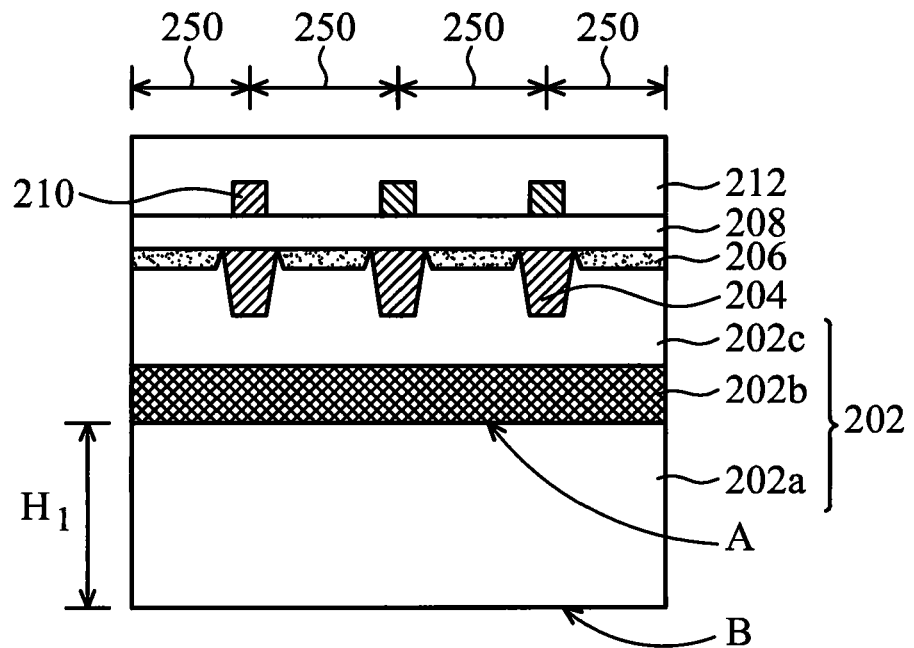
FIGS. 3-6 are cross sections showing a method for fabricating a biosensor device according to an embodiment of the invention.

As shown in FIG. 3, a fabricated biosensor structure is first provided, including a semiconductor on insulator (SOI) substrate 202 comprising a semiconductor layer 202a, an insulator layer 202b, and a semiconductor layer 202c sequentially stacked from bottom to top thereof. A plurality of isolation regions 204 is formed in the semiconductor layer 202c to thereby define a plurality of detection regions 250 thereover. A detection element 206 for detecting light of a first wavelength range is formed in the semiconductor layer 202c in corresponding detection regions 250 but is not limited thereto. The detection element 206 may also be formed over the semiconductor layer 202c of a corresponding detection region 250. Examples of the detection element 206 are charge-coupled devices (CCD), CMOS image sensors (CIS) and/or optical microelectromechanical systems (MEMS), incorporating photodiodes in active or passive arrangements. Herein, the semiconductor layer 202a can be, for example, a bulk silicon substrate having opposing surfaces A and B, wherein the surface A of the semiconductor layer 202a is physically connected with the insulating layer 202b and the surface B of the semiconductor layer 202a is exposed. The insulating layer 202b can be, for example, a dielectric interference filter having a layer sequence of two materials, such as a first material having high refractive index (n) of about 1.5~2.1 and a second material having a low refractive index (n) of about 1.4~1.8. In one preferred embodiment, the first material having a high refractive index can be, for example, silicon nitride, and the second material having a low refractive index, can be, for example, silicon dioxide. Therefore, the insulating layer 202b may function as an optical filter layer 114 to function as a bandpass filter. Herein, the semiconductor layer 202c can comprise, for example, silicon or silicon germanium. In addition, the semiconductor layer 202c is further doped with conductive type dopants, such as N or P type dopants. The semiconductor layer 202a is formed with a thickness $H_1$ of about 500~900 μm, the insulating layer 202b is formed with a thickness of about 500~3000 nm, and the semiconductor layer 202c is formed with a thickness of about 1~3 μm.

Moreover, as shown in FIG. 3, an interlayer dielectric (ILD) layer 208 is formed on the semiconductor layer 202c and covers the detection elements 206 therein. An interconnect structure comprising a dielectric layer 212 and a plurality of conductive elements 210 is provided over the semiconductor substrate 202c. The conductive elements 210 are respectively provided on or between the semiconductor substrate 202c at predetermined locations to electrically connect thereof to underlying detection elements 206 so that electromagnetic radiation (not shown) projected on the detection elements 206 will not be shielded by the existence of the conductive segments therein. A topmost dielectric layer 212 of the interconnecting structure may function as a passivation layer for protecting the biosensor device from moisture and abrasion during subsequent processes. Fabrication of the interconnect structure can be achieved by, for example, a damascene process incorporating copper metal and low dielectric constant (low-k) dielectric materials and is well known by those skilled in the art.

Figure 4:
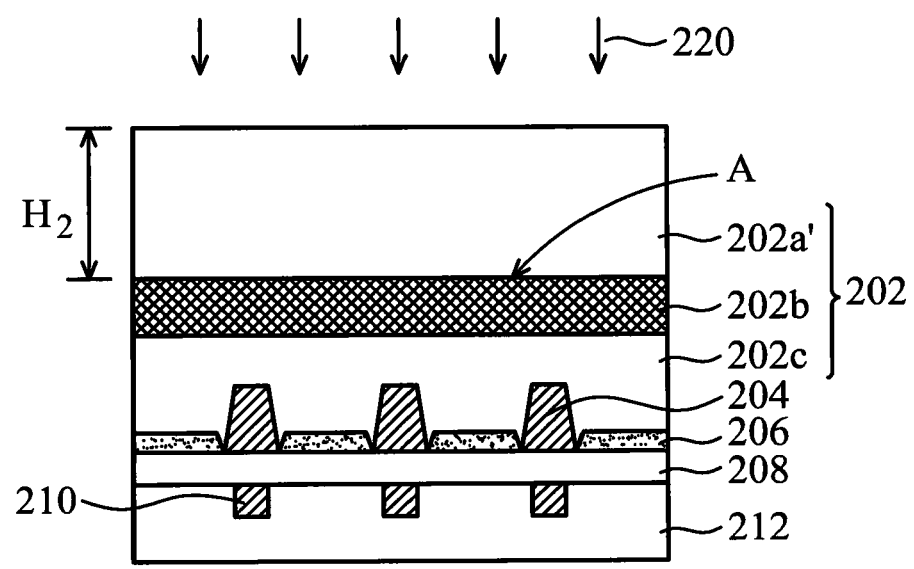

Moreover, as shown in FIG. 4, the semiconductor layer 202a in the fabricated biosensor structure is then reversed. The semiconductor layer 202a of the SOI substrate 202 is then thinned by a process 220 from a surface B thereof (See FIG. 3) to remove portions of the semiconductor layer 202a, thereby leaving a thinned semiconductor 202a' on the insulating layer 202b, having a thickness $H_2$ of about 20~50 μm. The process 220 can be, for example, a mechanical grinding, chemical mechanical polishing (CMP), dry etching and/or wet etching process.

Figure 5:
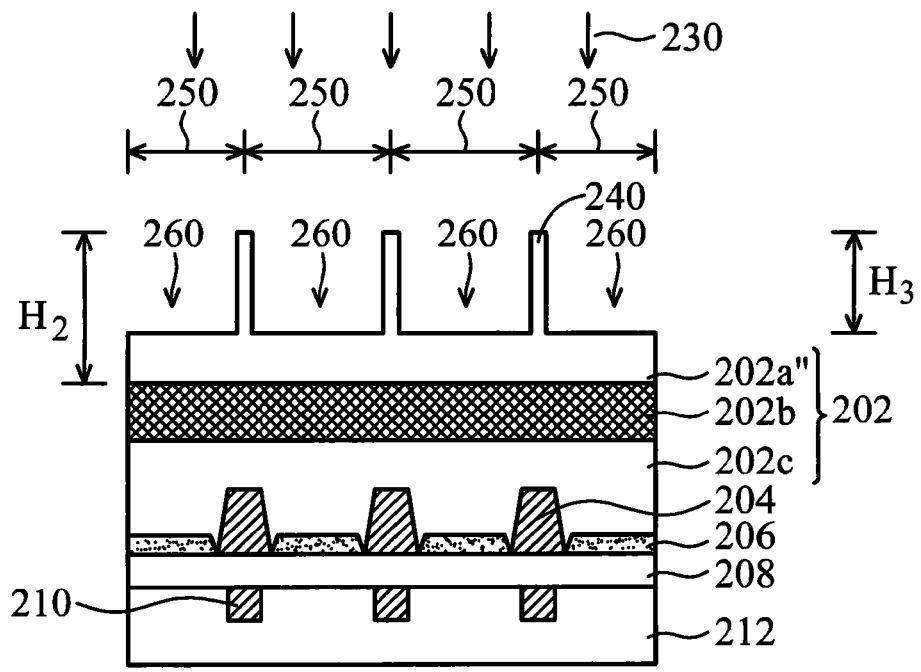

In addition, as shown in FIG. 5, the thinned semiconductor layer 202a' shown in FIG. 4 is then patterned by a process 230 to form a plurality of isolation walls 240 therein, thereby defining a plurality of micro-wells 260 and leaving a further thinned semiconductor layer 202a" over the SOI substrate 202. The process 230 can be, for example, a dry etching process whereby patterned masks (not shown) are formed over the thinned semiconductor layer 202a', as shown in FIG. 4. In one embodiment, each micro-well 260 is a recess having a depth $H_3$ of about 20~50 μm measured from a top surface of the isolation walls 240 to a top surface of the further thinned semiconductor layer 202a" exposed by the micro-wells 250.

Figure 6:
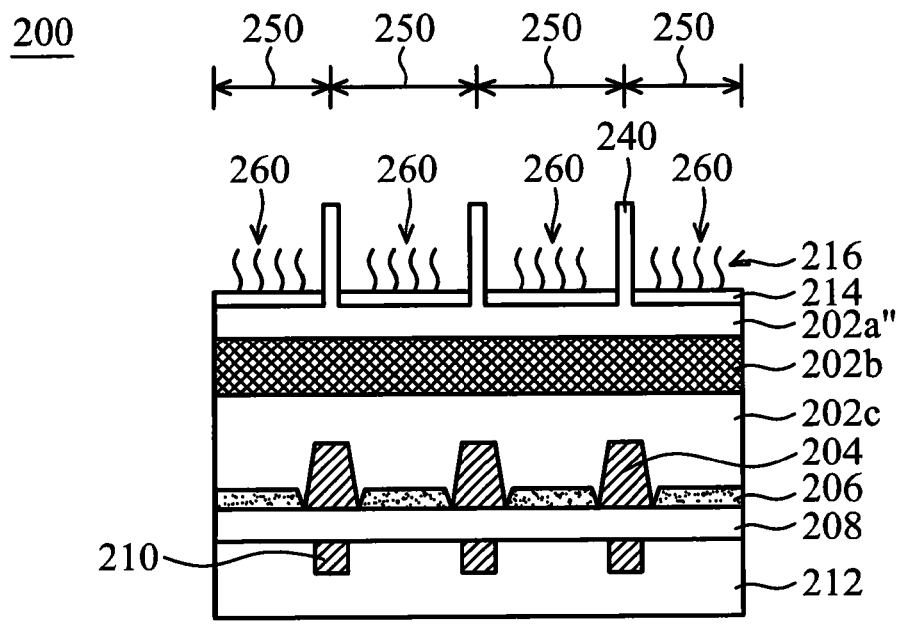

In FIG. 6, an immobilization layer 214 is formed over portions of the top surface of the further thinned semiconductor layer 202a" exposed by the micro-wells 250. The immobilization layer 214 can be, for example, a thin gold layer having a thickness of about 5~10 nm, and can be formed by methods such as e-beam evaporation. Next, a plurality of capsule molecules 216 is respectively provided over the top surface of the immobilization layer 214 formed in the well regions 250. The capsule molecules 216 can be, for example, DNA half strands, nucleic acids, peptides, or proteins which are capable of attaching molecules with predetermined markers such as fluorescence markers in a sample solution.

Thus, completing fabrication of an exemplary biosensor device 200 with robust micro-well structures and high fluorescence light collection efficiency as shown in FIG. 6. The operation of the biosensor device 200 is described as below. During biological analysis, the biosensor device 200 is brought in contact with a sample solution comprising molecules such as DNA half strands, nucleic acids, peptides, or proteins with predetermined markers such as fluorescence markers. The fluorescence markers can be determined by wavelength analysis of the fluorescence light reemitted by the fluorescence markers. After the molecules with predetermined markers such as fluorescence markers are attached to the capture molecules 216, the micro-wells 260 of the biosensor device 200 would be projected by emission light (not shown) of a second wavelength range. Thereafter, the capture molecules 216 attached with the molecules with predetermined markers such as fluorescence markers would reemit fluorescence light of a third wavelength range after excitation thereof by the emission light of the second range. Both of the emission lights of the second wavelength range and the reemitted fluorescence light of the third wavelength range are radiated in and pass through the transparent immobilization layer 214 and the further thinned semiconductor layer 202a", and pass to the optical filter layer (i.e. the insulating layer 202b). The optical filter layer functions as a blocking filter only for the emission light of the second wavelength range. Thus, the reemitted fluorescence light of the third wavelength range is transmitted through the optical filter layer and passes through the transparent semiconductor layer 202c, so that the reemitted fluorescence light may finally pass to the detection elements 206 arranged below the micro-wells 260 containing the capture molecules 216 attached with molecules with fluorescence markers. The detection elements 206 then detect the reemitted fluorescence light of the third wavelength range, wherein the detected reemitted fluorescence light of the third wavelength range is within the first wavelength range. As a result, a degree of molecular combinations are detected since the intensity of the detected fluorescence light corresponds to the number of detected molecular combinations. Emission light having the second wavelength range does not pass through the optical filter layer and cannot be detected in the detection elements 206. In this embodiment, the micro-wells 260 formed over the SOI substrate 202 are formed by patterning parts of the original semiconductor layer 202c (see FIG. 3) rather than formed by deposition and patterning of the photosensitive materials as that used in the biosensor device 100 illustrated in FIG. 1. Thus, the micro-wells 260 formed over the SOI substrate 202 will not collapsed when a sample solutions flows therein. Since the micro-wells 260 are integrated with the further thinned semiconductor layer 202a″, robust micro-well structures are thus formed and no residue overhangs as that illustrated in FIGS. 1 and 2 are formed over a top portion of the isolation walls 240. Thus, fluorescence light collect efficiency of the detection elements 206 is increased.

FIGS. 7-10 are schematic cross sections showing another exemplary method for fabricating a biosensor device with robust micro-well structures and high fluorescence light collection efficiency.

Figure 7:
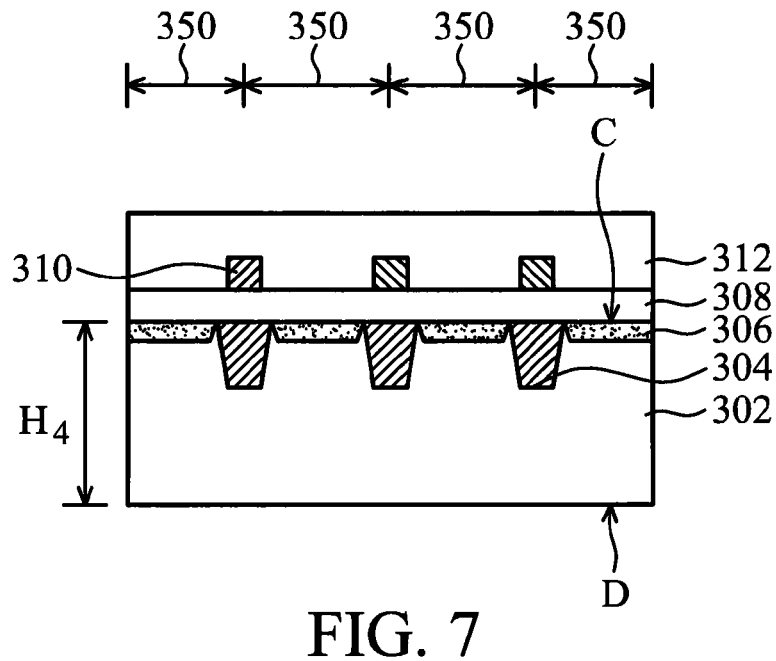
FIGS. 7-10 are schematic cross sections showing a method for fabricating a biosensor device according to another embodiment of the invention.

As shown in FIG. 7, a fabricated biosensor structure is first provided, including a substrate 302 made of bulk semiconductor materials such as bulk silicon. The substrate 302 is formed with opposing surfaces C and D, and a plurality of isolation regions 304 is formed in the substrate 302 from the surface C thereof to thereby define a plurality of detection regions 350 thereover. A detection element 306 for detecting light of a first wavelength range is formed in the substrate 302 in corresponding detection regions in the surface C, but is not limited thereto. The detection element 306 may also be formed over the surface C of the substrate 302 of a corresponding detection region 350. Examples of the detection element 306 are charge-coupled devices (CCD), CMOS image sensors (CIS) and/or optical microelectromechanical systems (MEMS), incorporating photodiodes in active or passive arrangements. In addition, the substrate 302 is further doped with conductivity type dopants, such as N or P type dopants. The substrate 302 is formed with a thickness $H_4$ of about 500~900 μm.

Moreover, as shown in FIG. 7, an interlayer dielectric (ILD) layer 308 is formed on the substrate 302 and covers the detection elements 306 therein. An interconnect structure comprising a dielectric layer 312 and a plurality of conductive elements 310 is provided over the semiconductor substrate 302. The conductive elements 310 are respectively provided on or between the semiconductor substrate 302 at predetermined locations to electrically connect thereto to underlying detection elements 306 so that electromagnetic radiation (not shown) projected on the detection elements 306 will not be shielded by the existence of the conductive segments therein. A topmost dielectric layer 312 of the interconnecting structure may function as a passivation layer for protecting the biosensor device from moisture and abrasion during subsequent processes. Fabrication of the interconnect structure can be achieved by, for example, a damascene process incorporating copper metal and low dielectric constant (low-k) dielectric materials and is well known by those skilled in the art.

Figure 8:
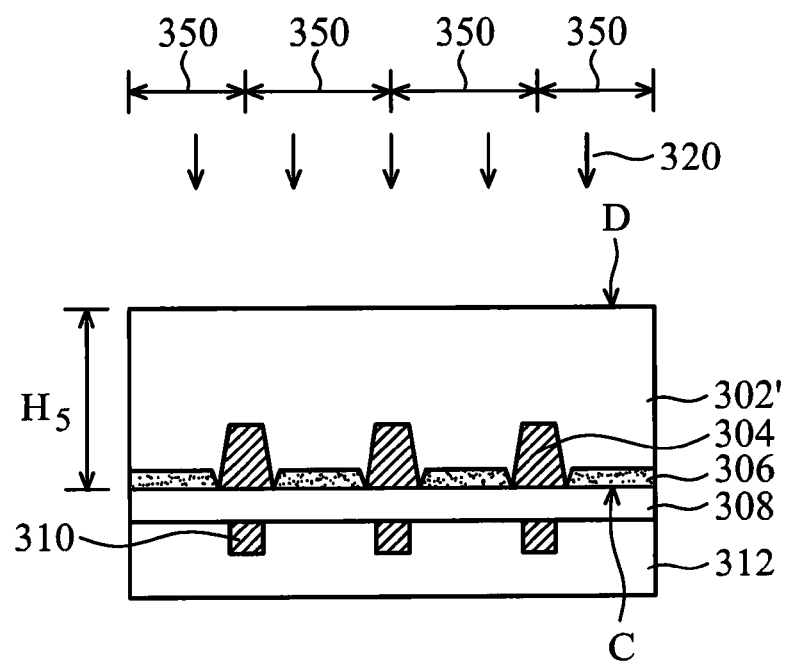

Moreover, as shown in FIG. 8, the substrate 302 in the fabricated biosensor structure is then reversed to expose the surface D thereof. The substrate 302 is then thinned by a process 320 from the surface D thereof to remove portions of the substrate 302, thereby leaving a thinned substrate 302a′, having a thickness $H_5$ of about 20~50 μm. The process 320 can be, for example, a mechanical grinding, chemical mechanical polishing (CMP), dry etching and/or wet etching process.

Figure 9:
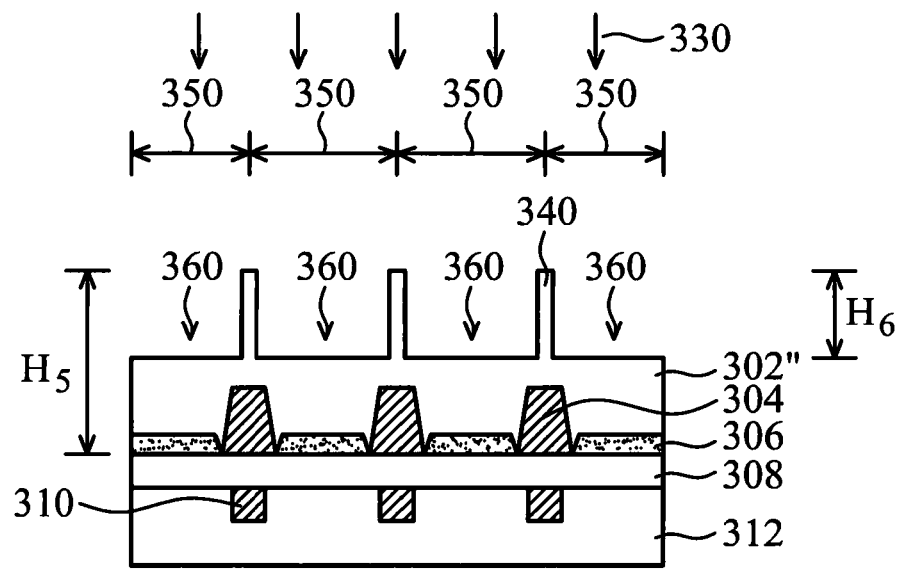

In addition, as shown in FIG. 9, the thinned substrate 302a′ shown in FIG. 9 is then patterned by a process 330 to form a plurality of isolation walls 340 therein, thereby defining a plurality of micro-wells 360 and leaving a further thinned substrate 302″. The process 330 can be, for example, a dry etching process using patterned masks (not shown) formed over the thinned substrate 302a′ shown in FIG. 8. In one embodiment, each micro-well 360 is a recess having a depth $H_6$ of about 20~50 μm_measured from a top surface of the isolation wall 340 to a top surface of the further thinned substrate 302a″ exposed by the micro-wells 360.

Figure 10:
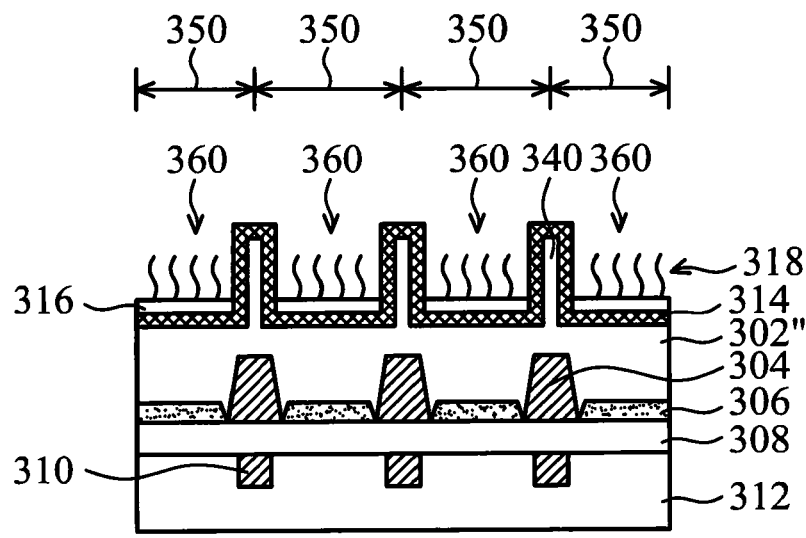

In FIG. 10, an optical filter layer 314 is conformably formed over the isolation walls 340 and the further thinned substrate 302″. The optical filter layer 314 can be, for example, a dielectric interference filter of a thickness of about 1 μm. The optical filter layer 314 can be formed by methods such as PVD, sputtering, PECVD and may have a layer sequence comprising two materials, such as a first material having high refractive index (n) of about 1.5~2.1 and a second material having a low refractive index (n) of about 1.4~1.8.

In one embodiment, the first material having high refractive index can be, for example, silicon nitride (n=2), and the second material having a low refractive index, can be, for example, silicon dioxide (n=1.5). Therefore, the optical filter layer 314 may function as a bandpass filter. An immobilization layer 316 is formed over portions of the top surface of the optical filter layer 314 exposed by the micro-wells 360. The immobilization layer 316 can be, for example, a thin gold layer having a thickness of about 5~10 nm, and can be formed by methods such as e-beam evaporation. Next, a plurality of capsule molecules 318 is respectively formed over the top surface of the immobilization layer 316 formed in the well regions 360. The capsule molecules 318 can be, for example, DNA half strands, nucleic acids, peptides, or proteins which are capable of attaching molecules with predetermined markers such as fluorescence markers in a sample solution.

Thus, completing fabrication of an exemplary biosensor device 300 with robust micro-well structures and high fluorescence light collection efficiency as shown in FIG. 10. The operation of the biosensor device 300 is described as below. During biological analysis, the biosensor device 300 is brought in contact with a sample solution comprising molecules such as DNA half strands, nucleic acids, peptides, or proteins with predetermined markers such as fluorescence markers. The fluorescence markers can be determined by wavelength analysis of the fluorescence light reemitted by the fluorescence markers. After the molecules with predetermined markers such as fluorescence markers are attached to the capture molecules 318, the micro-wells 360 of the biosensor device 300 would be projected by emission light (not shown) of a second wavelength range. Thereafter, the capture molecules 318 attached with the molecules with predetermined markers such as fluorescence markers would reemit fluorescence light of a third wavelength range after excitation thereof by the emission light of the second range. Both of the emission lights of the second wavelength range and the reemitted fluorescence light of the third wavelength range are radiated in and pass through the transparent immobilization layer 316, and pass to the optical filter layer 314.

The optical filter layer 314 functions as a blocking filter for the emission light of the second wavelength range. Thus, the reemitted fluorescence light of the third wavelength range is transitted through the optical filter layer 314 and passes through the transparent further thinned substrate 302″, so that the reemitted fluorescence light finally passes to the detection elements 306 arranged below the micro-wells 360 containing the capture molecules 318 attached with molecules with fluorescence markers The detection elements 306 then detect the reemitted fluorescence light of the third wavelength range, wherein the detected reemitted fluorescence light of the third wavelength range is within the first wavelength range. As a result, a degree of molecular combinations are detected since the intensity of the detected fluorescence light corresponds to the number of detected molecular combinations. Emission light having the second wavelength range does not pass through the optical filter layer and cannot be detected in the detection elements 206. In this embodiment, the micro-wells 360 formed over the further thinned substrate 302" are formed by the original semiconductor layer 302 (see FIG. 7) rather than the photosensitive materials as that used in the biosensor device 100 illustrated in FIG. 1. Thus, the micro-wells 360 formed over the further thinned substrate 302" will not collapse when a sample solution flows therein. Since the micro-wells 360 are integrated with the further thinned semiconductor layer 202a", robust micro-well structures are formed. Thus, residue overhangs as that illustrated in FIGS. 1 and 2 is not formed over a top portion of the isolation walls 340, thereby increasing fluorescence light collection efficiency of the detection elements 306.

The biosensor device 200 illustrated in FIG. 6 and the biosensor device 300 illustrated in FIG. 10 also have the following advantages. Referring to the biosensor device respectively illustrated in FIGS. 6 and 10, since a backside of the semiconductor substrate/layer without formation of the detection elements 206/306 are exposed and micro-wells 360 are formed thereover, emission light for biological analysis can be projected onto the detection elements 206/306 by passing along an optical path having minimal interference elements such as conductive interconnects 210/310 than that of the biosensor device illustrated in FIG. 1. Therefore, reduced optical interference and improved quantum efficiency of the detection elements 206/306 formed within such biosensor device can be achieved for small sized biosensor devices.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A biosensor device, comprising:
an interconnect structure;
a first semiconductor layer formed over the interconnect structure;
a plurality of detection elements formed in the first semiconductor layer;
an optical filter layer formed over and physically contacting the first semiconductor layer;
a second semiconductor layer formed over the optical filter layer, having opposing first and second surfaces, wherein the first surface physically contacts the optical filter layer;
a plurality of isolation walls formed over the second semiconductor layer from the second surface thereof, defining a plurality of micro-wells over the second semiconductor layer, wherein the isolation walls and the second semiconductor layer comprises the same material, and the micro-wells are correspondingly arranged with the detection elements;
an immobilization layer formed over the second semiconductor layer exposed by the micro-wells; and
a plurality of capture molecules formed over the immobilization layer in the mirco-wells.

2. The biosensor device as claimed in claim 1, wherein isolation wall elements, the second semiconductor layer, the optical filter layer, and the first semiconductor layer are portions of a semiconductor on insulator (SOI) substrate.

3. The biosensor device as claimed in claim 1, wherein the optical filter layer is a dielectric interference filter having a layer sequence comprising silicon dioxide and silicon nitride.

4. The biosensor device as claimed in claim 1, wherein the detection elements are CCD, CIS or optical MEMS devices.

5. The biosensor device as claimed in claim 1, wherein the capture molecules comprise DNA half strands, nucleic acids, peptides, or proteins.

6. The biosensor device as claimed in claim 1, wherein the immobilization layer comprises gold and has a thickness of about 5~10 nm.

7. The biosensor device as claimed in claim 1, wherein the micro-wells have a depth of about 20~50 μm from a top surface of the isolation walls to a top surface of the second semiconductor layer exposed by the micro-wells.

8. A biosensor device, comprising:
an interconnect structure;
a first semiconductor layer formed over the interconnect structure, having opposing first and second surfaces, wherein the first surface physically contacts the interconnect structure;
a plurality of detection elements formed in the first semiconductor layer from the first surface thereof;
a plurality of isolation walls formed over the second surface of the first semiconductor layer, defining a plurality of micro-wells over the first semiconductor layer, wherein the isolation walls and the first semiconductor layer comprises the same material, and the micro-wells are correspondingly arranged with the detection elements;
an optical filter layer conformably formed over the isolation walls and the second surface of the first semiconductor layer;
an immobilization layer formed over a portion of the optical filter layer exposed by the micro-wells; and
a plurality of capture molecules formed over the immobilization layer in the micro-wells.

9. The biosensor device as claimed in claim 8, wherein the first semiconductor layer comprises silicon.

10. The biosensor device as claimed in claim 8, wherein the optical filter layer is a dielectric interference filter having a layer sequence comprising silicon dioxide and silicon nitride.

11. The biosensor device as claimed in claim 8, wherein the detection elements comprise CCD, CIS or optical MEMS devices.

12. The biosensor device as claimed in claim 8, wherein the capture molecules comprise DNA half strands, nucleic acids, peptides, or proteins.

13. The biosensor device as claimed in claim 8, wherein the immobilization layer comprises gold and has a thickness of about 5~10 nm.

14. The biosensor device as claimed in claim 8, wherein the micro-wells have a depth of about 20~50 μm from a top surface of the isolation walls to the first semiconductor layer exposed by the micro-wells.

15. A biosensor device, comprising:
an interconnect structure;
a semiconductor substrate formed over the interconnect structure, having opposing first and second surfaces, wherein the first surface physically contacts the interconnect structure;
a plurality of detection elements formed in the semiconductor substrate from the first surface thereof;
a plurality of isolation walls formed over the second surface of the semiconductor substrate, defining a plurality of micro-wells over the semiconductor substrate, wherein the isolation walls and the semiconductor substrate comprises the same material, and the micro-wells are correspondingly arranged with the detection elements;

an immobilization layer formed over a portion of the second surface of the semiconductor substrate exposed by the micro-wells;

a plurality of capture molecules formed over the immobilization layer in the micro-wells; and an optical filter layer formed between the immobilization layer and the detection elements.

16. The biosensor device as claimed in claim 15, wherein the semiconductor substrate is a bulk semiconductor substrate.

17. The biosensor device as claimed in claim 16, wherein the optical filter layer is formed on the second surface of the semiconductor substrate exposed by the micro-wells, and the immobilization layer is formed on the optical filter layer.

18. The biosensor device as claimed in claim 15, wherein the semiconductor substrate is a semiconductor on insulator (SOI) substrate.

19. The biosensor device as claimed in claim 18, wherein the optical filter layer is integrated in the SOI substrate, and the immobilization layer is formed on the second surface of the SOI substrate.

* * * * *